United States Patent [19]

Moser et al.

[11] 4,126,440

[45] Nov. 21, 1978

[54] HYDROXAMIC ACID DERIVATIVES FOR REGULATING PLANT GROWTH

[75] Inventors: Hans Moser, Magden; Rolf Schurter, Binningen, both of Switzerland

[73] Assignee: Ciba-Geigy Corporation, Ardsley, N.Y.

[21] Appl. No.: 772,420

[22] Filed: Feb. 28, 1977

[30] Foreign Application Priority Data

Mar. 9, 1976 [CH] Switzerland ............. 2898/76
Jan. 7, 1977 [CH] Switzerland ............. 175/77

[51] Int. Cl.$^2$ ............. A01N 5/00; A01N 9/20; C07C 83/10
[52] U.S. Cl. ............. 71/76; 71/118; 260/500.5 H; 260/453 RW
[58] Field of Search ............. 71/118, 76; 260/453 RW, 260/500.5 H

[56] References Cited

U.S. PATENT DOCUMENTS

| | | | |
|---|---|---|---|
| 2,676,188 | 4/1954 | Bruce et al. | 260/559 |
| 3,442,945 | 5/1969 | Olin | 71/118 |
| 3,634,509 | 1/1972 | Yates et al. | 260/500.5 H |
| 3,718,805 | 1/1973 | Yates et al. | 71/115 |
| 3,907,544 | 9/1975 | Olin | 71/118 |
| 4,008,066 | 2/1977 | Moser | 71/76 |

FOREIGN PATENT DOCUMENTS 2,311,897  1/1973  Fed. Rep. of Germany.

OTHER PUBLICATIONS

Moser, Chem. Abst., vol. 84 (1976) 16991w.

*Primary Examiner*—Catherine L. Mills
*Attorney, Agent, or Firm*—Harry Falber

[57] ABSTRACT

Hydroxamic acid derivatives of the formula I shown hereinafter are effective plant growth retarding agents. They may be used on grasses, e.g., to prevent embankments from becoming overgrown by weeds and to impart to the stalks of cereal plants greater strength by effecting a reduction in height.

17 Claims, No Drawings

HYDROXAMIC ACID DERIVATIVES FOR REGULATING PLANT GROWTH

The present invention relates to novel hydroxamic acid derivatives, to processes for producing them, as well as to the composition retarding plant growth, and to a process for retarding and inhibiting plant growth with the aid of these novel compounds.

This narrow group of compounds has the general formula I

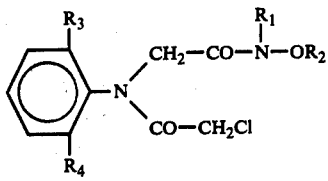

wherein
$R_1$ represents methyl or ethyl, and
$R_2$ represents hydrogen, methyl or ethyl, while
$R_3$ and $R_4$ independently of one another each represent methyl or ethyl.

It has been discovered that such hydroxamic acid derivatives surprisingly produce a plant-growth retardation which is extraordinarily advantageous for practical purposes, without any injurious effects on the plants treated in this manner. On the contrary, these acquire on treatment a better rigidity and a more intense green colouration. Representatives which structurally are bordering directly on the outler limits of the range of compounds embraced by the formula I likewise possess in some cases these properties that are described in more detail in the following, but they frequently do not possess them to the extent that would render them sufficiently effective for practical use, or to the extent that they could be used without damaging the plants.

Unlike a herbicidal effect, the effect that a substance retarding plant growth has on the plants has to be of such a nature that the treated plants suffer no damage. The compounds of the formula I satisfy this requirement to a high degree in the case of application to emerged plants. Particularly grasses growing wild and cultivated grasses on lawns as well as cereals are retarded in growth. In practice, it is possible both to prevent excessive weed infestation of railway embankments, of strips bordering highways, of slopes of river banks, of factory installations, etc., and to maintain intact the turf necessary for consolidation of the soil. Unlike after application of a herbicide, there occurs no destruction of the plants and hence no erosion of the soil. Keeping the vegetation short renders unnecessary the otherwise regularly required grass-cutting operations, which are problematic at difficulty accessible places, such as embankments, and which increase the risk of accidents where road traffic is circulating. Compounds of the formula I also inhibit however the growth of shrubs such as pivet, and the growth of lignifying plants such as blackberry; both being species of plants the proliferation of which frequently contributes towards the undermining of the foundations of railway tracks. In the case of varieties of cereals, such as in particular rye and barley and also wheat, the reduction in height (shortening of the internodal distance) results in a desired increase of the stalk's resistance to breaking. Crop losses often occurring as a result of flattening of the cereals owing to continuous rain or to hailstorms can be largely avoided.

Generally preferred are compounds of the formula I wherein $R_1$ and $R_2$ independently of one another represent methyl or ethyl, and $R_3$ and $R_4$ represent methyl.

The compounds of the formula I which are especially outstanding as growth inhibitors of grasses are those wherein $R_3$ and $R_4$ have the given meanings, whilst the sum of the carbon atoms of the two substituents $R_1$ and $R_2$ has the value three. To be mentioned, inter alia, are in particular the compounds given below

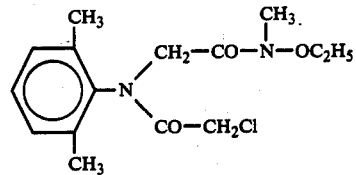

No. 3 and

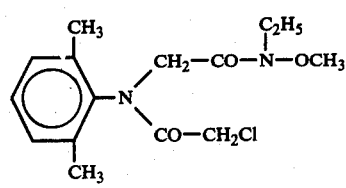

No. 5 as well as the compounds No. 9 and No. 11 subsequently listed.

By treatment with active substances of the formula I in the case of soya plants, the vegetative growth of the plants is retarded in favour of the generative growth (fruit setting). This is particularly surprising because as a rule a retardation of growth automatically results in a reduction of fruit setting. A smaller distance between rows of plants which have been treated with the present active substances and which therefore have a reduced breadth of growth leads to noticeably higher hectare yields.

A number of the compounds of the present invention result in practice also in a very effective inhibition of the growth of side shoots on tobacco plants.

The active substances of the formula I are stable compounds and have a duration of action of at least two months; in the cultivation however of plants such as soya beans, cereals or tobacco, the active substances are decomposed before the end of the cultivation season. The amounts applied are between 0.1 and 10 kg, preferably between 1.5 and 5 kg, of active substance per hectare.

The invention relates also to the use of compounds of the formula I for retarding plant growth, particularly the growth of grasses.

The following active substances are embraced by the formula I:

Table of active substances

1. N-chloroacetyl-2,6-dimethylanilino-acetic acid-(N'-methyl-N'-hydroxy)-amide, m.p. 136°–139° C;
2. N-chloroacetyl-2,6-dimethylanilino-acetic acid-(N'-methyl-N'-methoxy)-amide, m.p. 104°–106° C;
3. N-chloroacetyl-2,6-dimethylanilino-acetic acid-(N'-methyl-N'-ethoxy)-amide, m.p. 80°–82° C;
4. N-chloroacetyl-2,6-dimethylanilino-acetic acid-(N'-ethyl-N'-hydroxy)-amide, m.p. 154°–156° C;
5. N-chloroacetyl-2,6-dimethylanilino-acetic acid-(N'-ethyl-N'-methoxy)-amide, m.p. 88°–90° C;

6. N-chloroacetyl-2,6-dimethylanilino-acetic acid-(N'-ethyl-N'-ethoxy)-amide, m.p. 95°–98° C;
7. N-chloroacetyl-2-methyl-6-ethylanilino-acetic acid-(N'-methyl-N'-hydroxy)-amide, m.p. 88°–90° C;
8. N-chloroacetyl-2-methyl-6-ethylanilino-acetic acid-(N'-methyl-N'-methoxy)-amide, m.p. 82°–84° C;
9. N-chloroacetyl-2-methyl-6-ethylanilino-acetic acid-(N'-methyl-N'-ethoxy)-amide, m.p. 61°–63° C;
10. N-chloroacetyl-2-methyl-6-ethylanilino-acetic acid-(N'-ethyl-N'-hydroxy)-amide, m.p. 128°–130° C;
11. N-chloroacetyl-2-methyl-6-ethylanilino-acetic acid-(N'-ethyl-N'-methoxy)-amide, m.p. 64°–67° C;
12. N-chloroacetyl-2-methyl-6-ethylanilino-acetic acid-(N'-ethyl-N'-ethoxy)-amide, m.p. 80°–82°C;
13. N-chloroacetyl-2,6-diethylanilino-acetic acid-(N'-methyl-N'-hydroxy)-amide, m.p. 145°–147° C;
14. N-chloroacetyl-2,6-diethylanilino-acetic acid-(N'-methyl-N'-methoxy)-amide, m.p. 97° C;
15. N-chloroacetyl-2,6-diethylanilino-acetic acid-(N'-methyl-N'-ethoxy)-amide, m.p. 86°–88° C;
16. N-chloroacetyl-2,6-diethylanilino-acetic acid-(N'-ethyl-N'-hydroxy)-amide, m.p. 164°–167° C;
17. N-chloroacetyl-2,6-diethylanilino-acetic acid-(N'-ethyl-N'-methoxy)-amide, m.p. 98°–100° C;
18. N-chloroacetyl-2,6-diethylanilino-acetic acid-(N'-ethyl-N'-ethoxy)-amide, m.p. 128°–130° C.

2,6-Dialkylphenylaminoacetic acid esters as herbicides have become known from DT-OS NO. 2,212,268 (which corresponds to U.S. Pat. No. 3,780,090). However, the action even of those representatives emphasised as being preferred, such as N-(2,6-diethylphenyl)-N-chloroacetyl-aminoacetic acid ethyl ester, is unsatisfactory in many respects (plant selectivity, duration of action, applied amount). There is nothing stated concerning an action regulating plant growth, especially nothing concerning induced growth inhibition which occurs without disadvantageous consequences for the plant.

In DT-OS No. 2,311,897 (which is an equivalent to ZA-PS No. 73.00316) are likewise embraced and designed as herbicides a number of these representative compounds, including also N-(2,6-diethylphenyl)-N-chloroacetylaminoacetic acid ethyl ester. There are also stated however a large number of N-substituted phenylamines having exceptionally sharply varying structures, which not only fail to attain the herbicidal action of the above-mentioned type of compound, but fail in some cases to exhibit any herbicidal action at all, or even destroy useful plants and tolerate weeds. The reading of DT-OS No. 2,311,897 provides the person skilled in the art with the knowledge that within the very large group of N-(subst)phenyl-N-halocetyl-alkanecarboxylic acids or N-(subst)phenyl-N-halocetyl-alkanecarboxylic acid derivatives, only the group of N-haloacylated N-phenylacetic acid esters, mentioned also in DT-OS No. 2,212,268, is basically suitable as selective herbicides for practical purposes.

Furthermore, herbicidal N-acylated N-aminodalkyl-halogenoacetanilides are described in US-PS No. 3,830,841; and finally DT-OS No. 2,416,213 (or BE-PS No. 813,469) discloses ring-substituted N-chloroacetyl-phenylamino-acetamides as plantgrowth-regulating substances having simultaneously a clear herbicidal action.

It is therefore very surprising that the hydroxamic acid derivatives of the formula I produce in the case of many established plants a retardation of growth without any disadvantageous herbicidal effect.

The novel compounds of the formula I are produced according to the invention by reaction a phenylamino-acetamide of the formula II

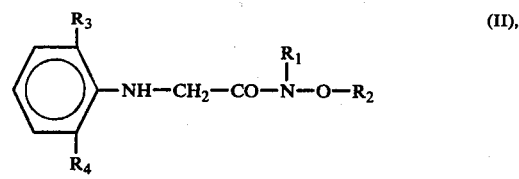

wherein $R_1$, $R_2$, $R_3$ and $R_4$ have the meanings given for formula I, with a chloroacetylating agent, preferably with an anhydride or halide of chloroacetic acid.

A further production process according to the present invention comprises converting an N-chloroacetyl-anilinoacetic acid of the formula III

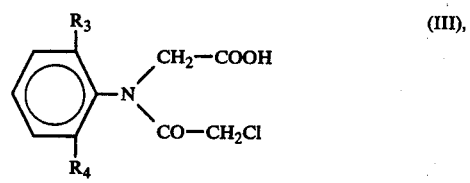

by the method, given in Helvetica Chimica Acta 34, p. 874 (1951), of the "mixed anhydrides", with hydroxylamine of the type $HN(R_1)$ $(OR_2)$ directly into compounds of the formula I.

The starting materials of the formula II are produced by customary methods, advantageously by one of the following methods:

a. the aniline on which the formula I is based, substituted by $R_3$ and $R_4$, is reacted with a haloacetamide of the formula Hal—$CH_2$—CO—N($R_1$) ($OR_2$), wherein "Hal" represents chlorine or bromine, in the presence of a weak to moderately strong base;

b. the aniline on which the formula I is based, substituted by $R_3$ and $R_4$, is reacted with a haloacetic acid ester of the formula Hal—$CH_2$—COO—alk, wherein "alk" represents an alkyl group, in the presence of a weak to moderately strong inorganic base, to form the intermediate IV

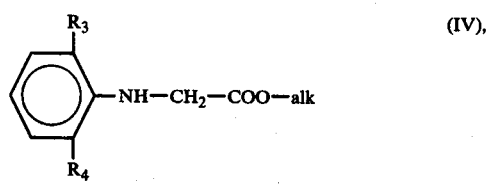

which is converted with excess hydroxylamine derivative $HN(R_1)$ $(OR_2)$ into the hydroxamic acid derivative of the formula II;

c. the aniline on which the formula I is based, substituted by $R_3$ and $R_4$, is reacted with, e.g., chloroacetonitrile to a cyanomethyl ester of the formula V

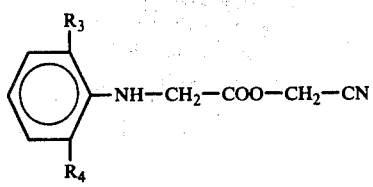

(V)

which can be readily converted with excess hydroxylamine derivative $HN(R_1)(OR_2)$ into compounds of the formula II.

The reactions can be performed in the presence or absence of solvents or diluents which are inert to the reactants. Those suitable are, for example, aliphatic, aromatic or halogenated hydrocarbons, such as benzene, toluene, xylenes, petroleum ether, chlorobenzene, methylene chloride, ethylene chloride or chloroform; also ethers such as dialkyl ether, dioxane or tetrahydrofuran; acetonitrile; dimethylsulphoxide or dimethylformamide, as well as mixtures of these solvents with each other.

Suitable chloroacetylating agents to be used are preferably chloroacetic acid anhydride and chloroacetic acid halides, such as chloroacetyl chloride or chloroacetyl bromide. The reaction can however also be performed with chloroacetic acid, in particular cases also with the esters thereof. The reaction temperatures are between 0° and 200° C, preferably between 20° and 100° C. With the use of chloroacetyl halides, the chloroacetylation is advantageously performed in the presence of an acid-binding agent, e.g. in the presence of a tertiary amine (such as triethylamine or pyridine) or of an inorganic base such as the oxide, hydroxide, hydrogen carbonate or carbonate of an alkali metal or alkaline-earth metal. It is also possible to use an excess of the aniline of the formula II as the acid-binding agent. The reaction is usually performed at normal pressure, if necessary at pressures up to 50 bars.

The following Examples illustrate the production of the starting materials and the processes according to the invention. The temperature values are given in degrees Centigrade.

PRODUCTION EXAMPLE 1 a. N-Chloroacetyl-2,6-dimethylanilinoacetic acid 36 g (0.2 mole) of 2,6-dimethylanilinoacetic acid, 400 ml of methylene chloride and 200 ml of 1N NaOH (0.2 mole) are placed into a flask with stirrer, and 17.5 ml (0.22 mole) of chloroacetic acid chloride is slowly added dropwise with stirring, the temperature being maintained at 20°–25° by cooling with ice-water. During the dropwise addition, there is formed a white precipitate. Stirring is continued for 30 minutes and the precipitate is then filtered off with suction; the precipitate is washed with cold water, well pressed out and subsequently dried over $P_2O_5$ in a desiccator. For the purpose of obtaining further amounts of final product, the methylene chloride phase is separated in a separating funnel, dried over $Na_2SO_4$ and concentrated in vacuo, and the crystalline residue is recrystallised from ethyl acetate. There is obtained a total amount of 44 g (86% of theory) of N-chloroacetyl-2,6-dimethylanilinoacetic acid, m.p. 160° (decomposition).

b. N-Chloroacetyl-2,6-dimethylanilinoacetic acid-(N'-methyl-N'-hydroxy)-amide (= compound 1)

25.6 g of N-chloroacetyl-2,6-dimethylanilinoacetic acid is suspended in 200 ml of benzene (abs.); 0.3 ml of pyridine and 10 ml of oxalyl chloride are added, and the reaction mixture is stirred overnight at room temperature. Stirring is then continued for 15 minutes at 50° C to complete the reaction. The almost clear solution is filtered and quickly concentrated in a rotary evaporator. The solid residue is dissolved in 100 ml of methylene chloride (= solution A).

There is separately prepared a second solution of 9.2 g of N-methylhydroxylamine oxalate in 50 ml of water, to which is added dropwise a mixture of 150 ml of ethanol and 42 ml of triethylamine. To this solution is then immediately added dropwise the solution A; stirring is continued for one hour at room temperature, and the reaction mixture is subsequently concentrated to dryness in the rotary evaporator. The residue is taken up in ethyl acetate, dried over $Na_2SO_4$ and freed from the solvent in vacuo. The crystalline final product is recrystallised from benzene to obtain 13.6 g, m.p. 136°–139°.

PRODUCTION EXAMPLE 2

N-Chloroacetyl-2,6-dimethylanilinoacetic acid-(N'-methyl-N'-ethoxy)-amide (= compound 3)

8.6 g of the compound No. 1 is dissolved in 30 ml of 1N NaOH. To this solution is added dropwise, with cooling and stirring, 4.3 ml of diethyl sulphate, and stirring is continued for 1 hour at room temperature. The precipitated oil is extracted with ethyl acetate, washed with water, dried over $Na_2SO_4$ and freed from the solvent in vacuo. There is thus obtained compound 3 in the form of light-yellow oil, which is dissolved in hot diisopropyl ether and crystallises on cooling, m.p. 80°–82°.

PRODUCTION EXAMPLE 3

N-Chloracetyl-2,6-dimethylanilinoacetic acid-(N'-ethyl-N'-methoxy)-amide (= compound 5)

25.6 g of N-chloroacetyl-2,6-dimethylanilinoacetic acid is suspended in 200 ml of benzene (abs.); there are added 0.3 ml of pyridine and 10 ml of oxalyl chloride and stirring is continued overnight at room temperature. Stirring is then performed for a further 15 minutes at 50° in order to complete the reaction. The almost clear solution is filtered and quickly concentrated in the rotary evaporator. The solid residue is dissolved in 100 ml of methylene chloride. The solution thus obtained is added dropwise at 5°– 10° to a second solution consisting of 7.5 g of N-ethyl-O-methyl-hydroxylamine, 100 ml of methylene chloride and 14 ml of triethylamine. After 1 hours's stirring at room temperature, the solution is diluted with 300 ml of methylene chloride; it is then extracted by shaking with small amounts of water, dried over $Na_2SO_4$ and concentrated by evaporation. The oily final product (18.5 g) crystallises from diisopropyl ether, m.p. 88°–90°.

PRODUCTION EXAMPLE 4 a. 2,6-dimethylanilinoacetic acid cyanomethyl ester 17.9 g of 2,6-dimethylanilinoacetic acid is refluxed, with stirring, in 150 ml of ethyl acetate with 14 ml of triethylamine and 7.6 ml of chloroacetonitrile for 3 hours. After cooling, the precipitated triethylamine hydrochloride is separated by filtration. The ethyl acetate solution is successively extracted with water, with 10% NaHCO$_3$ solution and with saturated sodium chloride solution. The acetic acid solution is dried over sodium sulphate, and the solvent is distilled off in vacuo to leave a brown oil, which is crystallised from diisoprpyl ether. There is obtained in this manner 11.2 g of cyanomethyl ester, m.p. 65°–67°.

b. 2,6-Dimethylanilinoacetic acid-N'-metyl-N'-methoxy amide 11 g of 2,6-dimetylaniloacetic acid cyanomethyl ester is heated with 6.1 g of N,O-dimethyl-hydroxylamine for 16 hours at 100° in a bomb tube. After cooling, the black coloured reaction mixture is taken up in ether; it is treated with active charcoal, filtered and concentrated by evaporation. The residue is fractionally distilled under high vacuum to obtain 6.5 g of 2,6-dimethylanilinoacetic acid-N'-methyl-N'-methoxy amide, b.p. 126°/0.01 mm Hg.

c. N-Chloroacetyl-2,6-dimethylanilinoacetic acid-(N'-methyl-N'-methoxy)-amide (= compound 2)

25.6 g (0.1 mole) of N-chloroacetyl-2,6-dimethylanilinoacetic acid according to Example 1a, dissolved in 150 ml of anhydrous tetrahydrofuran, is precooled to 15° in a flask with stirrrer. there is then added, with stirring, 26.18 ml (0.11 mole) of tri-n-butylamine; the clear solution is cooled to 0°, and 10.8 ml (0.11 mole) of 97% chloroformic acid ethyl ester is slowly added dropwise, with the temperature during the dropwise addition being held between 5° and 7°. Stirring is then slowly continued at the same temperature for a further 20 minutes. There is subsequently added dropwise 6.7 ml (0.11 mole) of methoxy-methylamine at 5°–7°, whereupon a slight evolution of CO$_2$ occurs. After the dropwise addition, the cooling bath is removed. The evolution of CO$_2$ becomes more intense above 10°. The reaction mixture is further stirred firstly for 30 minutes at room temperature and then for 15 minutes at an internal temperature of 35°–40°. After filtration, the reaction mixture is concentrated in vacuo to yield a yellow oil, which is taken up in ethyl acetate and then successively extracted with water, 2N hydrochloric acid, water, 10% NaHCO$_3$ solution, water and saturated sodium chloride solution. The ethyl acetate solution purified in this manner is dried over Na$_2$SO$_4$ and concentrated in vacuo. The resulting yellow oil is crystallised from diisopropyl ether to obtain 13.6 g (45.5% of theory) of N-chloroacetyl-2,6-dimethylanilinoacetic acid-N'-methyl-N'-methoxy amide, m.p. 104°–106°.

Compositions according to the invention are produced in a manner known per se by the intimate mixing and grinding of active substances of the general formula I with suitable carriers and/or distributing agents, optionally with the addition of anti-foaming agents, wetting agents, dispersing agents and/or solvents all inert to the active substances. The active substances can be made up and applied in the following forms:
  solid preparations: dusts, scattering agents, granules (coated granules, impregnated granules and homogeneous granules);
  water-dispersible concentrates of active substance: wettable powders, pastes, emulsions and emulsion concentrates;
  liquid preparations: solutions.

The concentration of active substance in the compositions according to the invention is 1 to 80 per cent by weight; the active substances can however also be applied at a low concentration, for example at a concentration of about 0.01 to 1%.

Other active substances or compositions advantageous in agricultural chemistry can be added to the described compositions according to the invention. To broaden their sphere of action, the novel compositions can thus contain, besides the stated compounds of the general formula I, for example insecticides, fungicides, bactericides, fungistatics, bacteriostatics, nematocides or herbicides.

Granulate

The following substances are used to produce a 5% granulate:
  5 parts of one of the active substances of the formula I,
  0.25 part of epichlorohydrin,
  0.25 part of cetyl polyglycol ether,
  3.50 parts of polyethylene glycol,
  91 parts of kaolin (particle size 0.3 – 0.8 mm).

The active substance is mixed with epichlorohydrin and dissolved with 6 parts of acetone; the polyethylene glycol and cetyl polyglycol ether are then added. the solution obtained is sprayed onto kaolin, and the acetone is evaporated off in vacuo.

Wettable powder

The following constituents are used to produce (a) a 70% wettable powder and (b) a 10% wettable powder:

(a)

70 parts of one of the active substances of the formula I,
5 parts of sodium dibutyl-naphthalene sulphonate,
3 parts of naphthalenesulphonic acid/phenolsulphonic acid/formaldehyde condensate 3:2:1,
10 parts of kaolin,
12 parts of Champagne chalk;

(b)

10 parts of N-chloroacetyl-2,6-dimethylanilinoacetic acid-N'-methyl-N'-ethoxyamide,
3 parts of a mixture of the sodium salts of saturated fatty alcohol sulphates,
5 parts of naphthalenesulphonic acid/formaldehyde condensate,
82 parts of kaolin.

The given active substance is absorbed onto the appropriate carriers (kaolin and chalk) and the material is subsequently mixed and ground. Wettable powders having excellent wetting and suspension properties are obtained. It is possible to prepare from such wettable powders, by dilution with water, suspensions containing 0.1 – 8% of active substance, which are suitable, e.g., for the spraying of crops of cultivated plants, lawns or vegetation on embankments.

Paste

The following substances are used to produce a 45% paste:
  45 parts of N-chloroacetyl-2,6-dimethylanilinoacetic acid N'-ethyl-N'-methoxyamide or of one of the other stated active substances of the formula I,
  5 parts of sodium aluminium silicate,
  14 parts of cetyl polyglycol ether having 8 moles of ethylene oxide, 1 part of oleyl polyglycol ether having 5 moles of ethylene oxide,
2 parts of spindle oil,
10 parts of polyethylene glycol,
23 parts of water.

The active substance is intimately mixed and ground with the additives in suitable devices to obtain a paste, from which can be produced, by dilution with water, suspensions of the desired concentration.

Emulsion concentrate

The following constituents are mixed together to produce a 25% emulsion concentrate:
25 parts of an active substance of the formula I,
5 parts of a mixture of nonylphenolpolyoxyethylene or calcium dodecylbenzenesulphonate,
35 parts of 3,3,5-trimethyl-2-cyclohexen-1-one,
35 parts of dimethylformamide.

This concentrate can be diluted with water to give emulsions of suitable concentration, e.g. a concentration of 0.1 to 10%.

Biological Examples

Growth retardation in the case of grasses

Seeds of the grasses *Lolium perenne, Poa pratensis, Festuca ovina* and *Dactylis glomerata* were sown in plastic trays containing a soil/peat/sand mixture (6:3:1) and watered in the usual manner. The emerged grasses were cut back weekly to a height of 4 cm; and 40 days after sowing and 1 day after the last cutting they were sprayed with aqueous spray liquors of the active substances of the formula I. The amount of active substance was equivalent to 5 kg of active substance per hectare. The growth of the grasses was evaluated 10 and 21 days after application of the active substances, according to the following linear scale of values:
1 = severe retardation (no further growth from time of application, 0%),
9 = no retardation (100% growth, as in the case of the untreated control specimens).

The active substances of the formula I effected a pronounced retardation of growth to 70% or less of the normal height of growth. The compounds Nos. 6, 8, 9, 11, 15 and 17 produced a reduction of growth to about 50% the normal thenormal height. An even more pronounced reduction of growth to less than 50% was effected by the compounds Nos. 3 and 5.

Retardation of growth in the case of cereals

Spring wheat (*Triticum aestivum*), spring barley (*Hordeum vulgare*) and rice (*Oryza sativa*) were sown in plastic bowls containing sterilised soil, and grown in a greenhouse. The wheat and barley were treated with spray liquors of the active substances 5 days after sowing, and the rice 12 days after sowing. The application to the leaves corresponded to 6 and 2 kg, respectively, of active substance per hectare (soil application = 500 and 100 ml of liquor per pot). After application of the active substances, the rice bowls were covered with water up to 3 cm above the soil.

An evaluation was carried out 7 and 21 days after application. All the compounds of the formula I produced a clear shortening and simultaneous strengthening of the stalks.

Regulation of the growth of soya bean plants
(Growth retardation, branching, pod setting).

Soya beans of the variety "Hark", "Grosskorn" or "Lee 68" were sown in a soil/peat/sand mixture (6:3:1) in 11 cm pots with 4–5 seeds per pot in a greenhouse at about 25°. After emergence, the plants were thinned out down to the two strongest plants per pot, which were then tied up. As soon as the plants had developed three unfolded trifoliate leaves, the preparation of active substance was sprayed on until the surface of the leaves was uniformly wetted. The concentrations of active substance were 1000, 500 and 100 ppm of active substance. After being transferred to an air-conditioned chamber, the plants were watered with a sprinkling tube and subsequently received a nutrient solution once weekly. An evaluation was made 14 and 28 days after application. The compounds of the formula I produced inhibition of the vegetative growth. On the other hand, it was observed that branching and on the setting on the treated plants were normal.

We claim:

1. Hydroxamic acid derivatives of the formula I

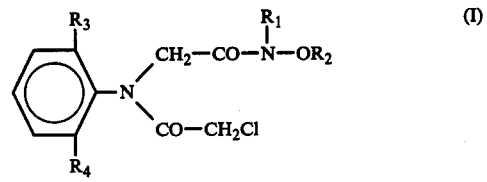

wherein
$R_1$ represents methyl or ethyl, and
$R_2$ represents hydrogen, methyl or ethyl, while
$R_3$ and $R_4$ independently of one another each represent methyl or ethyl.

2. Compounds according to claim 1, wherein the sum of the carbon atoms in the substituents $R_1$ and $R_2$ has the value three, while $R_3$ and $R_4$ represent methyl or ethyl.

3. Compounds according to claim 1, wherein $R_1$ and $R_2$ represent methyl or ethyl, and $R_3$ and $R_4$ represent methyl.

4. N-Chloroacetyl-2,6-dimethylanilinoacetic acid-N'-methyl-N'-ethoxy-amide according to claim 1.

5. N-Chloroacetyl-2,6-dimethylanilinoacetic acid-N'-ethyl-N'-methoxy-amide according to claim 1.

6. N-Chloroacetyl-2-methyl-6-ethylanilinoacetic acid-N'-methyl-N'-ethoxy-amide according to claim 1.

7. N-Chloroacetyl-2-methyl-6-ethylanilinoacetic acid-N'-ethyl-N'-methoxy-amide according to claim 1.

8. A composition for retarding and inhibiting plant growth, which composition contains as active substance a non-phytotoxic, plant growth retarding amount of a hydroxamic acid derivative of the formula I according to claim 1

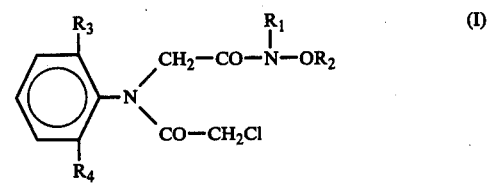

wherein
$R_1$ represents methyl or ethyl, and
$R_2$ represents hydrogen, methyl or ethyl, while
$R_3$ and $R_4$ independently of one another each represent methyl or ethyl,
together with a suitable carrier therefor.

9. Composition according to claim 8, which contains compounds of the formula I wherein the sum of the carbon atoms in the substituents $R_1$ and $R_2$ has the value three, while $R_3$ and $R_4$ represent methyl or ethyl.

10. Composition according to claim 8, which contains compounds of the formula I wherein $R_1$ and $R_2$ represent methyl or ethyl, and $R_3$ and $R_4$ represent methyl.

11. Composition according to claim 8, which contains N-chloroacetyl-2,6-dimethylanilinoacetic acid-N'-methyl-N'-ethoxyamide.

12. Composition according to claim 8, which contains N-chloroacetyl-2,6-dimethylanilinoacetic acid-N'-ethyl-N'-methoxy-amide.

13. Composition according to claim 8, which contains N-chloroacetyl-2-methyl-6-ethylanilinoacetic acid-N'-methyl-N'-ethoxyamide.

14. Composition according to claim 8, which contains N-chloroacetyl-2-methyl-6-ethylanilinoacetic acid-N'-ethyl-N'-methoxyamide.

15. A process for retarding and inhibiting plant growth, which comprises applying to established crops of plants a non-phytotoxic, plant growth retarding amount of a compound according to claim 1.

16. Process according to claim 15, wherein grasses and gramineous plants are treated.

17. Process according to claim 15, wherein crops of soya bean are treated.

* * * * *